United States Patent [19]
Nicholson

[11] Patent Number: 5,509,801
[45] Date of Patent: Apr. 23, 1996

[54] ORAL THERAPEUTIC APPARATUS FOR COOLING ORAL TISSUES

[76] Inventor: James A. Nicholson, 120 S. 28th Ave., Hattiesburg, Miss. 39401

[21] Appl. No.: 453,879

[22] Filed: May 30, 1995

Related U.S. Application Data

[62] Division of Ser. No. 100,279, Aug. 2, 1993.
[51] Int. Cl.⁶ ................................. A61C 17/02
[52] U.S. Cl. .............. 433/80; 433/35; 601/139; 601/164; 601/165
[58] Field of Search ............. 433/35, 80; 601/139, 601/164, 165; 424/435, 78.05; 514/887

[56] References Cited

FOREIGN PATENT DOCUMENTS 0048609  9/1986  U.S.S.R. .

*Primary Examiner*—Carlos A. Azpuru
*Attorney, Agent, or Firm*—Dowell & Dowell

[57] ABSTRACT

An oral therapeutic apparatus and a method of using the oral device for treating a patient undergoing a chemotherapy treatment are disclosed wherein the oral device is formed to be insertable within the patient's mouth and receive a circulated cooling medium to continuously and uniformly cool the patient's oral tissues including the gums, cheeks, tongue, roof and base of the mouth, to prevent the oral tissues from absorbing the chemotherapy agent to thereby prevent inflammation and oral sores.

20 Claims, 2 Drawing Sheets

ORAL THERAPEUTIC APPARATUS FOR COOLING ORAL TISSUES

This application is a division of application Ser. No. 08/100,279, filed Aug. 02/1993 now abandoned.

BACKGROUND OF THE INVENTION

1. Field of the Invention

This invention is directed to an oral therapeutic apparatus comprising an oral device that is used to treat cancer patients undergoing chemotherapy treatments and a method of using the oral device. The oral device is formed to be insertable within a patient's mouth and receive a circulated cooling medium to cool the patient's oral tissues including the gums cheeks, tongue, roof and base of the mouth, to reduce the absorption of chemotherapy agent.

2. Description of the Related Art

One of the most limiting side effects associated with chemotherapy treatments of cancer patients is the condition characterized by severe inflammation of the oral mucous membrane tissues known as mucositis. This inflammation produces oral sores that are so painful for the patient that frequently the chemotherapy treatments must be weakened or even discontinued before they are completed. As a result, cancer patients oftentimes can not be given the necessary amount of chemotherapy to effectively treat their conditions.

It has been known, however, that keeping the oral tissues cold during chemotherapy treatments causes vasoconstriction of the associated blood vessels which reduces the amount of chemotherapy agent flowing into this tissue. The known method of cooling the oral tissues comprises periodically placing ice within the patient's mouth during the administration of the chemotherapy agent. This method lessens the formation of oral sores for short treatment periods of less than about one hour.

Although the known method of cooling the oral tissues has been acceptable for short treatments, it is impractical for extended chemotherapy treatments that may continue for extended periods, for at least the following reasons. First, it is quite difficult for the patient to sleep because the rapidly melting ice must be constantly replaced. Second, and, more importantly, it fails to constantly and uniformly cool all of the oral tissues that are prone to form inflammation. The known method does not maintain the oral tissues at a constant desired temperature for the duration of extended treatments, and mucositis and oral sores inevitably form and become a limiting problem that forces the chemotherapy dose to be reduced or the treatment discontinued. Although the patient may be able to withstand the lessened chemotherapy treatment, its effectiveness is limited and the cancer may grow at an uncontrollable rate despite the treatment.

Thus, in view of the inadequacies of the known method, there has been a need for an oral therapeutic apparatus, and a method of using the device, for effectively cooling selected oral tissues to reduce absorption of the chemotherapy agent and the subsequent formation of inflammation and oral sores, throughout extended periods of chemotherapy treatment. Such a device would reduce or eliminate the problem that have not been overcome by the known method and have reduced the effectiveness of previous chemotherapy treatments. Furthermore, there has been a need for an oral device that remains comfortable to the patient throughout the length of any treatment so that relaxation and even sleep can be obtained.

SUMMARY OF THE INVENTION

The present invention has been made in view of the above inadequacies of the prior art and has as an object to provide an oral therapeutic apparatus that comprises an oral device which is insertable in the mouth of a patient undergoing a chemotherapy treatment to prevent the formation of inflammation and oral sores, and thus enable the patient to receive full treatments at effective doses.

It is another object of the present invention to provide an oral device which conforms closely to the patient's mouth so that the device remains comfortable to the patient during the treatment, and that receives a cooling medium which uniformly cools the oral tissues to reduce the absorption of the chemotherapy agent and subsequent formation of inflammation and oral sores.

To achieve the objects of the invention, as embodied and broadly described herein, the present invention comprises an apparatus for reducing oral tissue inflammation of a patient being subjected to a chemotherapy treatment, which comprises an oral therapeutic device having an outer contour that conforms to the patient's mouth and contacts the patient's cheeks, gums, tongue, and roof and base of the mouth. The device contains a cooling medium which is preferably circulated therethrough by a supply source which maintains the cooling medium at the desired temperature to prevent warming of the device during the duration of the chemotherapy treatment.

DETAILED DESCRIPTION OF THE PREFERRED EMBODIMENT

The present invention will now be described in detail with reference to the drawings.

Figure 1:
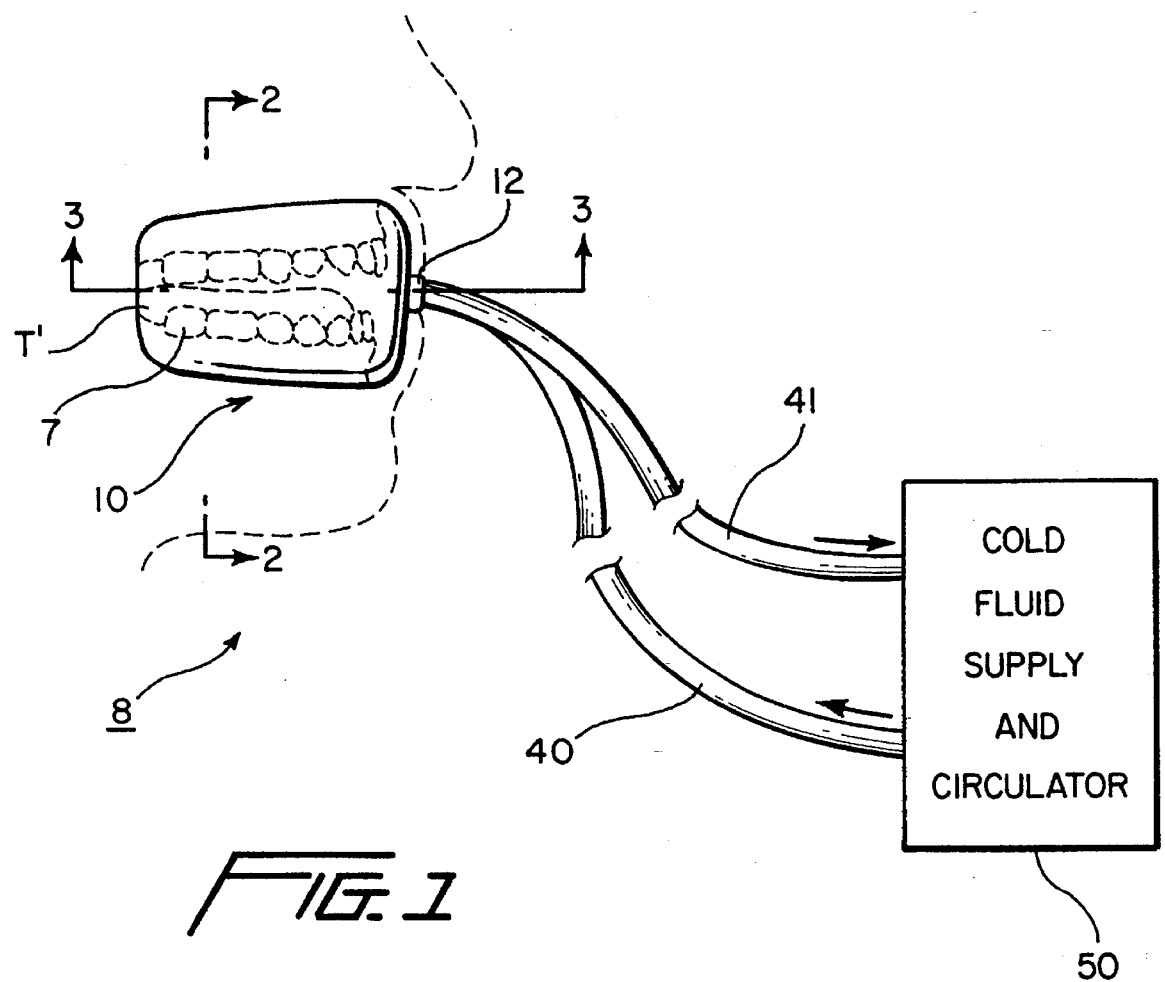
FIG. 1 is an illustrational view of an oral therapeutic apparatus in accordance with the invention comprising an oral device located within the mouth of an individual undergoing a chemotherapy treatment.
Figure 2:
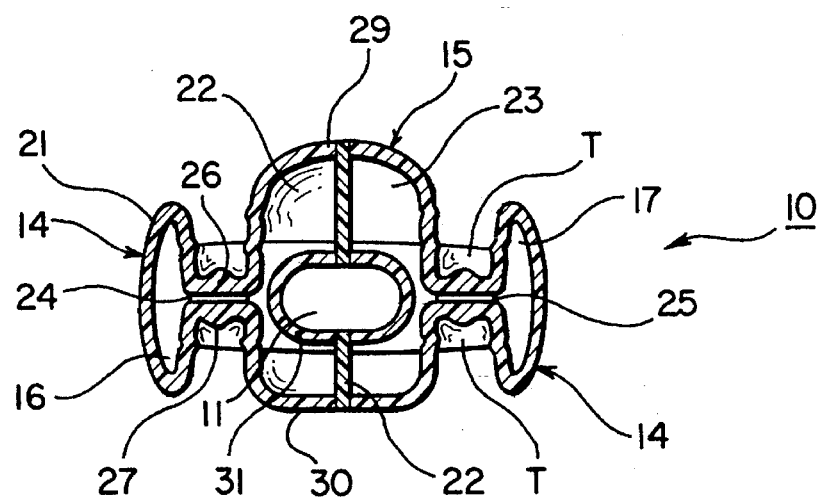
FIG. 2 is a cross-sectional view taken in the direction of line 2—2 of FIG. 1.
Figure 3:
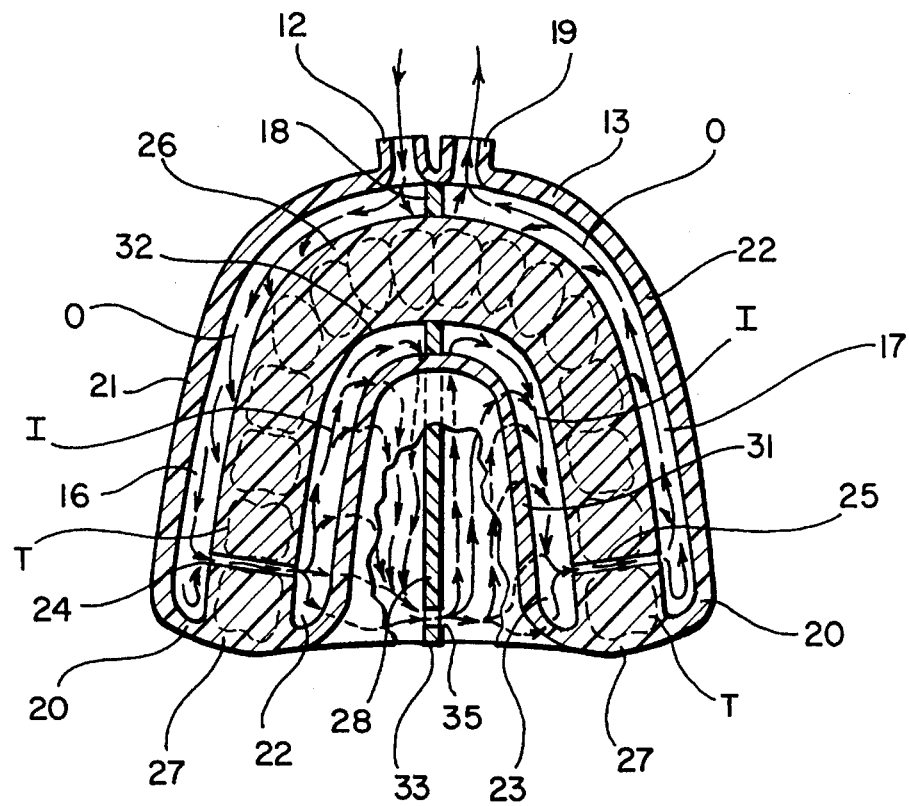
FIG. 3 is a cross-sectional view that is partially broken away and taken in the direction of line 3—3 of FIG. 1, illustrating the flow pattern of cooling medium through the oral device.

FIG. 1 illustrates an oral therapeutic apparatus 8 in accordance with the present invention comprising an oral device 10 which is located within the mouth of a patient undergoing a chemotherapy treatment. As depicted in FIGS. 2 and 3, the therapeutic device is engaged by the upper and lower teeth, T, of the patient, and includes a tongue opening 11 in which the patient's tongue, T' is received.

The oral device 10 is composed of a material that is pliable and biocompatible with the patient's oral tissues and can be used to form the device from an impression of the patient's mouth as will be described in greater detail below. Suitable materials include, for example, acrylic, plastic, silicon and rubber.

The therapeutic device is formed by first making stone casts of the patient's teeth along with a bite registration. The casts are mounted on an articulator to simulate the patient's occlusal, and the articulator is adjusted to form a 4–6 mm vertical occlusal space.

Next, a buildup is initiated with the preferred therapeutic device. A wax pattern is fabricated and added to the buildup, which pattern defines the inner and outer bladders and interconnection with the fluid inlet and fluid outlet. The preferred material is added to enclose the wax pattern as well as the entrance and exit of the tongue opening. The preferred material is allowed to harden or cure either at room temperature, or at an elevated temperature within a heating source such as a pressure pot.

The hardened device is then placed in boiling water or within a hot atmosphere such as in an oven to melt the wax pattern, and the wax is poured out to produce a hollow device. The device is then finished, shaped and contoured. Finally, to assure that the outer surface of the finished device properly conforms to the contour of the patient's mouth, it is placed therein to verify an accurate fit. The device must fit comfortably and not extend so far into the patient's mouth that it causes the patient to gag.

A cooling medium is supplied to the oral device at a desired temperature by a supply source 50. The supply source includes a pump for continuously circulating the cooling medium. The supply source further includes means for cooling the circulated cooling medium so that it is maintained at the necessary temperature to cool the oral tissues throughout the chemotherapy treatment.

A fluid inlet tube 40 is connected at one end to a fluid inlet port 12 formed at a front wall 13 of the oral device (see FIG. 3) and at the opposite end to the supply source 50. The therapeutic device is formed to contact and cool selected oral tissues within the patient's mouth. The cooling medium cools the therapeutic device which functions as a heat sink for heat generated in the oral tissues. The cooling medium is preferably circulated through the therapeutic device so that heat is continuously transferred away from the oral tissues and the device, to keep the oral tissues cold and prevent the device from significantly warming during the chemotherapy treatment. Significant warming of the therapeutic device would allow inflammation and oral sores to form and consequently force the treatment to be reduced or discontinued.

Water is the preferred cooling medium because it has desirable heat transfer properties; however, other cooling mediums such as solutions of water and alcohol may optionally be used. Preferably, the cooling medium is maintained at a temperature of approximately 0° C to approximately 5° C.

In those instances when the cooling medium is circulated, it is caused to flow through the therapeutic device, and return to the supply source through the fluid outlet line 41 which is connected to the fluid outlet port 19 of the device (see FIG. 3). The supply source is preferably connected to a water line which provides a continuous supply of water. It may optionally contain a fixed supply of a cooling medium which is repeatedly circulated through the therapeutic device.

For relatively short length chemotherapy treatments where warming of the therapeutic device is a less significant problem, the cooling medium may be enclosed in the oral device and not be circulated. In such instances, the therapeutic device may be filled with a cold fluid, and then sealed and placed within the patient's mouth. Alternatively, the cooling medium may be introduced into the device, which is sealed and cooled in a refrigerator or the like to the proper temperature. The cooling medium may be a non-toxic gel or a like substance that can maintain its initial temperature for the duration of the chemotherapy treatment.

As illustrated in FIGS. 2 and 3, the oral device comprises an outer bladder 14 which is spaced outwardly relative to a relatively smaller inner bladder 15. The outer bladder defines an outer cavity which includes a first outer chamber 16 and a second outer chamber 17 which are separated from each other by a barrier wall 18. The barrier wall extends between the fluid inlet and outlet ports and prevents the cooling medium from flowing directly between the outer chambers 16 and 17.

The outer chambers 16 and 17 have a generally elongated cross-sectional shape, and extend rearwardly from the outer wall to the rear wall portions 20 of the outer bladder 14. The outer chambers are spaced at a substantially constant distance from the outer surfaces of the side walls 21 and 22, which contact the patient's respective cheeks, and follow the outer contour of the outer bladder. This constant spacing of the outer chambers assures uniform heat transfer away from the patient's cheeks to thereby reduce capillary size and subsequent inflammation of the cheek tissues to occur.

The outer chambers communicate with upper and lower cavities 22 and 23 located within the inner bladder 15. The cooling medium flows from the first outer chamber 16 into the first inner chamber through a first channel 24, and from the second inner chamber into the second outer chamber 17 through a second channel 25. The first and second channels are located within an intermediate bite portion of the device which is located between and integral with the outer bladder and the inner bladder as best shown in FIG. 2. The bite portion includes a top wall 26 and a bottom wall 27, and is solid except for the two channels. The patient's upper teeth engage the top wall 26, and the associated gums contact outer surfaces of the inner and outer bladders, as shown in FIG. 2. Similarly, the bottom teeth engage the bottom wall 27, and the associated gums contact the outer walls of the inner and outer bladders. FIG. 3 illustrates the first channel 24 and the second channel 25 positioned between the patient's rear molars when the oral device is placed in the patient's mouth.

The first and second inner cavities 22 and 23 are separated from each other by an inner wall 28 that is connected to the upper wall 29 and the lower wall 30 of the inner bladder. Intermediate the upper and lower walls, the inner wall is connected to an interior wall 31 that defines the tongue opening 11. As shown in FIG. 3, the inner wall is connected to the front wall 32 and the rear wall 33 of the inner bladder.

The inner wall 28 includes a lower passage 34 and a vertically spaced upper passage 35 shown in FIG. 3, which are located proximate to the rear wall 33. The passages are provided so that cooling fluid flows between the inner cavities at a controlled rate. The upper and lower passages are sized to assure an adequate rate of fluid flow between the inner cavities to constantly transfer heat away from the surrounding oral tissues.

The flow pattern of the cooling medium through the apparatus and therapeutic device will now be described with reference to FIGS. 3 and 4 which include arrows representing the direction of flow through the various portions of the device. After the therapeutic device is inserted in a patient's mouth, the supply source 50 is actuated to supply cooling fluid through the fluid inlet tube 40 and into the therapeutic device through the inlet port 12. The cooling fluid fills the first outer chamber 16 and cools its surrounding wall 21, which contacts one of the patient's cheeks and cools the oral tissues thereof and also cools the gums along the upper and lower jaw.

The cooling medium flows from the first outer chamber 16 through the first channel 24 and into the first inner cavity 22. It fills the first inner cavity and cools a surrounding portion of the upper wall 29 which contacts the roof of the mouth, a portion of the lower wall 30 which contacts the base of the mouth, and a portion of the interior wall 31 contacting the tongue. The cooled wall surrounding the first inner cavity also cools the patient's gums which are in contact therewith as shown in FIG. 2. The cooling medium flows through the lower passage 34 and upper passage 35 of the inner wall 28 and into the second inner cavity 23. The cooling medium cools the remainder of the wall of the inner bladder 15 and the interior wall 31. These wall portions cool the surrounding roof and base of the mouth, and the tongue as well as the adjacent gums. After the second inner chamber is filled, the cooling medium flows through the second passage 25 and into the second outer chamber 17. The cooling fluid fills this outer chamber and cools its wall which contacts and cools the other cheek and the gums and exits the therapeutic device through the outlet port 19. The cooling medium returns to the supply-source through the outlet tube 41, and is recirculated through the therapeutic device.

Figure 4:
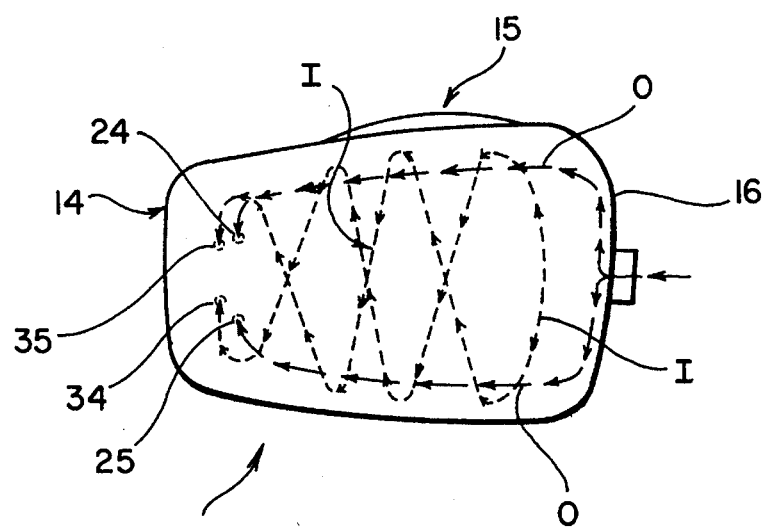
FIG. 4 is a side elevational view of an oral device in accordance with the present invention illustrating the flow pattern of the cooling medium through the inner and outer chambers thereof.

In FIG. 4, the arrows, O, represent the general direction of fluid flow through the outer chambers, and the arrows, I, represent the general direction of fluid flow through the inner cavities.

The therapeutic device in accordance with the present invention constantly and uniformly cools the patient's cheeks, gums, tongue, and roof and base of the mouth. Because it closely conforms to the contour of the patient's mouth, it can be used for extensive treatments without causing discomfort. Furthermore, its uniform and constant cooling action reduces or prevents the formation of inflammation and oral sores throughout extended chemotherapy treatments.

The foregoing description of the preferred embodiment of the invention has been presented to illustrate the principles of the invention and not to limit the invention to the particular embodiment illustrated. It is intended that the scope of the invention be defined by all of the embodiments encompassed within the following claims, and their equivalents.

What is claimed is:

1. An apparatus for cooling a patient's oral tissues while undergoing medical or dental treatment, comprising an oral therapeutic device having a body having imperforate wall portions which define a plurality of chambers in which a cooling medium may be retained, said body being formed of a biocompatible material which is shaped to be insertable in, and conform to, the contour of a patient's mouth.

2. That apparatus of claim 1, in which said body includes a pair of outer wall portions defining at least one outer chamber, an intermediate bite portion extending from said pair of outer wall portions, and a pair of inner wall portions defining at least one inner chamber connected to said bite portion whereby a cooling medium may be contained in said inner and outer chambers.

3. The apparatus of claim 2, in which said at least one outer chamber is of a size to be in a heat exchange relationship with both the upper and lower gums and inside cheek of a patient.

4. The apparatus of claim 3 in which said at least one inner chamber includes upper and lower portions which are oriented so as to be disposed on opposite sides of the patient's tongue when said apparatus is positioned within the patient's mouth.

5. The apparatus of claim 4 including circulating means for circulation of the cooling medium through said inner and outer chambers.

6. The apparatus of claim 5 including an inlet means and outlet means communicating with said at least one outer chamber, and said circulating means being connected to said inlet means and said outlet means.

7. The apparatus of claim 6 including at least one passageway through said bite portion so as to communicate said at least one outer chamber with said at least one inner chamber.

8. The apparatus of claim 7 including a pair of outer chambers, said inlet means communicating with one of said outer chambers and said outlet means communicating with the other of said outer chambers, a first passageway communicating said first outer chamber with said at least one inner chamber and a second passageway for connecting said at least one inner chamber to said other outer chamber.

9. The apparatus of claim 8 including an opening in said body defined by one of said inner walls, said opening being of a size to cooperatively receive a portion of the patient's tongue therein.

10. The apparatus of claim 9 including a pair of inner chambers each having upper and lower portions, upper and lower interior walls separating said upper portions and said lower portions from one another, and at least one opening in each of said interior walls for allowing flow of the cooling medium between said inner chambers.

11. The apparatus of claim 1, wherein said device includes outer walls defining at least one cavity for receiving the cooling medium, and an interior wall which defines an opening for receiving the patient's tongue.

12. The apparatus of claim 11, wherein said outer walls contact the patient's cheeks, gums and roof and base of the mouth.

13. The apparatus of claim 11, further comprising a fluid inlet and a fluid outlet extending into said device and communicating with said cavity.

14. The apparatus of claim 13, further comprising means for supplying the cooling medium through said fluid inlet and into said cavity and for receiving the cooling medium from said fluid outlet.

15. The apparatus of claim 14, wherein said biocompatible material is pliable.

16. The apparatus of claim 15, wherein said device includes an inner cavity, an outer cavity and channels through which said inner and outer cavities communicate.

17. The apparatus of claim 16, wherein said outer cavity includes a first outer chamber and a second outer chamber, and an outer wall separating said first and second outer chambers and preventing direct fluid flow therebetween.

18. The apparatus of claim 17, wherein said inner cavity includes a first inner chamber and a second inner chamber, and an inner wall separating said first and second inner chambers and defining at least one fluid passage therethrough.

19. The apparatus of claim 18, wherein said biocompatible material is pliable.

20. The apparatus of claim 10, wherein said biocompatible material is pliable.

* * * * *